(12) United States Patent
Scott et al.

(10) Patent No.: US 10,156,513 B2
(45) Date of Patent: Dec. 18, 2018

(54) REDUCED VOLUME SPECTROSCOPIC SAMPLE CELL

(71) Applicant: SpectraSensors, Inc., Rancho Cucamonga, CA (US)

(72) Inventors: Peter Scott, Glendora, CA (US); Alfred Feitisch, Los Gatos, CA (US); Peter Dorn, Rancho Cucamonga, CA (US); Adam S. Chaimowitz, Rancho Cucamonga, CA (US); Hsu-Hung Huang, Rancho Cucamonga, CA (US); Mathias Schrempel, Alta Loma, CA (US); Lutz Keller, Fontana, CA (US)

(73) Assignee: SpectraSensors, Inc., Rancho Cucamonga, CA (US)

( * ) Notice: Subject to any disclaimer, the term of this patent is extended or adjusted under 35 U.S.C. 154(b) by 0 days.

(21) Appl. No.: 14/807,859

(22) Filed: Jul. 23, 2015

(65) Prior Publication Data

US 2016/0153890 A1    Jun. 2, 2016

Related U.S. Application Data

(63) Continuation of application No. 14/073,711, filed on Nov. 6, 2013, now Pat. No. 9,109,951.

(51) Int. Cl.
*G01N 21/31* (2006.01)
*G01N 21/03* (2006.01)
(Continued)

(52) U.S. Cl.
CPC .............. *G01N 21/031* (2013.01); *G01J 3/42* (2013.01); *G01N 21/01* (2013.01);
(Continued)

(58) Field of Classification Search
CPC ............ G01N 33/564; G01N 2800/24; G01N 33/6893; G01N 33/57423;
(Continued)

(56) References Cited

U.S. PATENT DOCUMENTS 3,515,491 A * 6/1970 Emary .................... G01N 21/03
356/246
4,440,497 A * 4/1984 Carey ..................... G01N 21/05
356/246

(Continued)

FOREIGN PATENT DOCUMENTS

CN           1932479 A    3/2007
CN        202008463 U   10/2011
(Continued)

*Primary Examiner* — Michael P Stafira
(74) *Attorney, Agent, or Firm* — Mintz Levin Cohn Ferris Glovsky and Popeo, P.C.

(57) ABSTRACT

A sample cell can be designed to minimize excess gas volume. Described features can be advantageous in reducing an amount of gas required to flow through the sample cell during spectroscopic measurements, and in reducing a time (e.g. a total volume of gas) required to flush the cell between sampling events. In some examples, contours of the inners surfaces of the sample cell that contact the contained gas can be shaped, dimensioned, etc. such that a maximum clearance distance is provided between the inner surfaces at one or more locations. Systems, methods, and articles, etc. are described.

20 Claims, 9 Drawing Sheets

(51) Int. Cl.
*G01J 3/42* (2006.01)
*G01N 21/27* (2006.01)
*G01N 21/01* (2006.01)
*G01N 21/05* (2006.01)

(52) U.S. Cl.
CPC ......... *G01N 21/0303* (2013.01); *G01N 21/05* (2013.01); *G01N 21/27* (2013.01); *G01J 2003/423* (2013.01); *G01N 2021/0307* (2013.01); *G01N 2201/06113* (2013.01)

(58) Field of Classification Search
CPC ....... G01N 33/57407; G01N 33/57492; G01N 2500/04; G01N 33/574; G01N 33/505; G01N 2333/54; G01N 2333/7155; G01N 2800/205; G01N 33/57438
See application file for complete search history.

(56) References Cited

U.S. PATENT DOCUMENTS

| | | | |
|---|---|---|---|
| 5,220,402 A | 6/1993 | Harvey | |
| 5,574,232 A | 11/1996 | Davidson et al. | |
| 5,726,752 A | 3/1998 | Uno et al. | |
| 7,005,090 B2* | 2/2006 | Mueller | G01N 21/05 264/1.25 |
| 7,263,871 B2* | 9/2007 | Selker | G01N 21/1702 73/24.02 |
| 7,352,463 B2* | 4/2008 | Bounaix | G01N 21/031 356/437 |
| 8,111,391 B2* | 2/2012 | Mark | G01N 21/0317 257/678 |
| 8,154,727 B2* | 4/2012 | Dreyer | G01J 3/02 356/432 |
| 9,212,990 B1* | 12/2015 | Muraviev | G01J 3/0205 |
| 2003/0076491 A1* | 4/2003 | Mueller | G01N 21/05 356/246 |
| 2005/0117152 A1 | 6/2005 | Barnikol et al. | |
| 2006/0119851 A1* | 6/2006 | Bounaix | G01N 21/031 356/437 |
| 2007/0047599 A1* | 3/2007 | Wysocki | B82Y 20/00 372/20 |
| 2008/0225296 A1* | 9/2008 | Liu | G01J 3/433 356/437 |
| 2011/0164251 A1* | 7/2011 | Richter | G01N 21/031 356/440 |
| 2013/0188189 A1* | 7/2013 | Carson | G01N 21/33 356/437 |

FOREIGN PATENT DOCUMENTS

JP        H08 29323 A    2/1996
WO    WO-2004/023114 A1    3/2004

* cited by examiner

REDUCED VOLUME SPECTROSCOPIC SAMPLE CELL

CROSS REFERENCE TO RELATED APPLICATION

This is a continuation of U.S. application Ser. No. 14/073,711 filed Nov. 6, 2013 entitled REDUCED VOLUME SPECTROSCOPIC SAMPLE CELL, the disclosure of which is incorporated herein by reference.

TECHNICAL FIELD

The subject matter described herein relates to spectroscopic analysis, for example for use in detection, quantification, or the like of one or more analyte compounds.

BACKGROUND

Spectroscopic analysis generally relies on detection and quantification of emission, absorption, or scattering of radiation by matter. In the case of gas-phase spectroscopy, the emission, absorption, or scattering of radiation occurs by individual molecules of one or more compounds present along a radiation path between a radiation source and a detector. At least some of the radiation transmitted along this path can be absorbed or scattered, or other radiation can be emitted by the molecules in the radiation path. The wavelength of the absorbed, scattered, or emitted light generally is determined by the particular energy transition occurring to the molecules of one or more emitting or absorbing compounds in the radiation path. For example, in infrared spectroscopy, discrete energy quanta are absorbed by molecules due to excitation of vibrational or rotational transitions of the intra-molecular bonds.

Some uses of spectroscopic analysis techniques involve characterizing the presence and/or concentration of one or more target analyte compounds in a gas sample. Analyzers based on spectroscopic analysis are used in a variety of applications, including but not limited to process monitoring, process control, energy content metering, detection of chemical contaminants in gas streams, and the like. These applications generally involve repeated, sequential analysis of a flowing gas stream to detect and/or quantify one or more compounds in the gas stream. A typical configuration of such an analyzer receives a flowing supply of the gas stream into a sample volume through which a radiation path between one or more sources and one or more detectors is directed one or more times. In some examples, one or more mirrors are included in the radiation path such that the radiation path traverses at least part of the sample volume more than once.

A sample volume can in some examples be at least partially enclosed in a sample cell through which the radiation path passes at least once. It can be desirable to maintain the flow rate of the supplied gas stream through the sample cell (or other sample volume) at a sufficient flow rate to prevent sample contamination by mixing of one or more other gases (e.g., ambient air, etc.) with the sample gas, as well as to provide pressure and temperature stability to the sample gas for an accurate measurement. Flow rate control can also be desirable for preventing uncontrolled or excessive releases of potentially toxic or unhealthy or environmentally undesirable gases into the atmosphere. Flow rate control can furthermore be important to achieve improved response times to changes in the gas stream.

In various spectroscopic analyzer implementations, the structure and shape of a sample cell can be constrained by mechanical considerations. For example, a sample cell can desirably meet one or more structural requirements necessary to maintain a relative position of a radiation source and a detector to improve calibration accuracy and fidelity in gas measurement applications. Movement of the detector relative to the radiation source or other changes in the radiation path between the radiation source and the detector can lead to deviations in analyzer performance, analytical errors, lack of reproducibility, etc. Sample cell design can also include considerations relating to temperature stability and control, gas flow control, and the like.

SUMMARY

Consistent with one or more aspects of the current subject matter, a spectroscopic sample cell can have physical dimensions chosen to provide an uninterrupted radiation path (e.g. a beam) between a radiation source and a detector while also reducing the excess gas volume in the sample cell that is not traversed by the beam.

In one aspect, a sample cell includes at least one opening for receiving a beam from a radiation source into an inner volume of the sample cell and for allowing the beam to exit the sample cell to contact a detector. Inner surfaces of the sample cell define a boundary of the inner volume. The inner surfaces include a location at which a maximum clearance distance for gas flow is less than approximately 75 times a characteristic dimension of a cross section of the beam.

In another interrelated aspect, a method includes receiving a beam from a radiation source into an inner volume of a sample cell and allowing the beam to exit the sample cell to contact a detector, defining a boundary of the inner volume with inner surfaces, and passing a flowing gas stream through the sample cell. The inner surfaces include a location at which a maximum clearance distance for gas flow is less than approximately 75 times a characteristic dimension of a cross section of the beam In still another interrelated aspect, a system includes a radiation source, a detector, and a sample cell. The sample cell includes at least one opening for receiving a beam from a radiation source into an inner volume of the sample cell and for allowing the beam to exit the sample cell to contact a detector. Inner surfaces of the sample cell define a boundary of the inner volume. The inner surfaces include a location at which a maximum clearance distance for gas flow is less than approximately 75 times a characteristic dimension of a cross section of the beam.

In yet another interrelated aspect, an apparatus includes inner surfaces of an outer wall at least partially defining an inner volume through which a beam of a radiation source is received, at least one mirror element at each of two opposing ends in the inner volume and an insert within the inner volume sized and positioned at a location intermediate the mirror elements. The insert reduces a clearance distance for gas flowing through the inner volume at locations within the inner volume at which the beam does not pass.

In optional variations, one or more of the following features can optionally be included, in any feasible combination, in a method, a system, an article of manufacture, or the like. The sample cell can include an insert that occupies an excess gas volume within the inner volume through which the beam does not pass, and an insert surface of the insert can include at least part of the location. The location can include at least one baffle feature that creates the maximum clearance distance for gas flow in at least one dimension. The insert can include one or more of a flat insert, a conical insert, a hyperbolic insert, a trapezoidal insert, a cylindrical insert, and a hollow rod insert. The insert can include a component volume configured to house one or more of an electronics component, a wiring component, a flow control component, a flow path and a scrubber component of a spectroscopy system. The insert can include a gas conduit to feed gas to an inlet of the inner volume. The gas conduit can include a liquid drain to divert liquids carried within the gas conduit away from the inner volume. The sample cell can be configured as a Herriott cell, a tubular enclosure, a rectangular enclosure, a White cell, and a Pfund cell.

The inner volume of the sample cell can be at least partially contained within a gas passageway having at least one side wall and a length over which the beam travels at least once. The gas passageway can be formed within a block by one or more of a boring process and a channeling process. The block can include one or more parts that form the gas passageway. The gas passageway can have a cross-sectional shape, and over at least part of the length, the cross sectional shape can include at least one of a circle, an ellipse, and a rectangle. The gas passageway can be disposed such that the beam travels through the gas passageway from the source located near a first end of the gas passageway to the detector located near a second end of the gas passageway. The beam can be reflected at least once from the at least one side wall as the beam travels through the gas passageway. The gas passageway can be substantially collinear with an axis of propagation of the beam.

As noted above, the maximum clearance distance can be approximately 75 times a characteristic dimension of a cross section of the beam. In optional variations, the maximum clearance distance can be in a range of less than approximately 65 times the characteristic dimension of the cross section of the beam, or alternatively in a range of approximately 3 to 10 times the characteristic dimension of the cross section of the beam, in a range of approximately 3 to 20 times the characteristic dimension of the cross section of the beam, in a range of approximately 3 to 50 times the characteristic dimension of the cross section of the beam, in a range of approximately 3 to 30 times the characteristic dimension of the cross section of the beam, in a range of approximately 3 to 40 times the characteristic dimension of the cross section of the beam, or in a range of approximately 3 to 60 times the characteristic dimension of the cross section of the beam.

The sample cell can include at least one reflective surface from which the beam is reflected at least one time. The at least one reflective surface can include a mirror disposed at one end of the inner volume.

The details of one or more variations of the subject matter described herein are set forth in the accompanying drawings and the description below. Other features and advantages of the subject matter described herein will be apparent from the description and drawings, and from the claims. It should be noted that the current subject matter contemplates both a flowing sample gas stream and a static sample gas from which a sample gas volume can be withdrawn. The terms "sample volume," "sample gas volume," "gas volume," and the like as used herein can refer to either a flowing volume or a static, batch volume of gas unless the context in which such a term is used requires a narrower interpretation.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Figure 1:
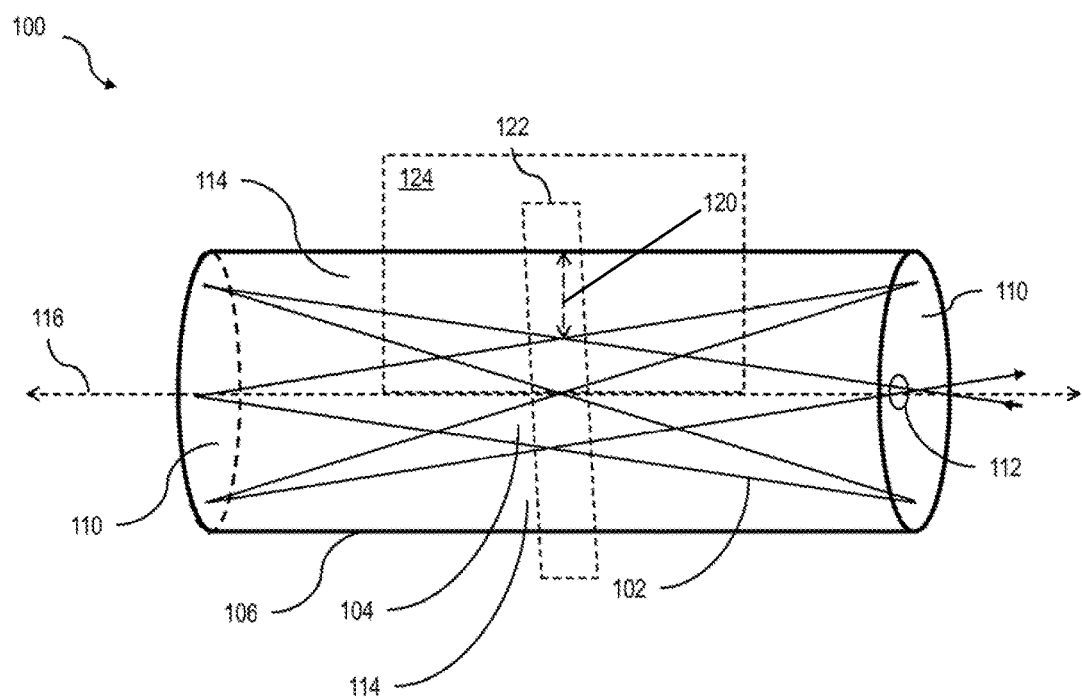
FIG. 1 shows a side view isometric diagram illustrating features of a sample cell.

Sample cells and gas analysis approaches consistent with the descriptions herein can be used in conjunction with a variety of spectroscopic methods and systems. In some implementations of the current subject matter, a tunable diode laser (TDL) analyzer, a tunable quantum cascade laser (TQCL) analyzer, a tunable intraband cascade laser (TICL) analyzer, a Raman Spectroscopy Analyzer, or the like can be used with a sample cell configured as a tubular enclosure, an optical waveguide enclosure, a prism enclosure, a Pfund cell, a White cell, a Herriott cell, or a modification or combination of any of those cells or enclosures. The sample cell can include one or more ports for the entrance and exit of a radiation path (e.g. a beam) to and from a sample gas that is at least partially contained within the sample cell. The beam interacts with the sample gas to cause absorption, scattering, or emission of radiation, which can be quantified by one or more detectors. The path of the beam through the sample gas can advantageously be of a suitable length to allow for sufficient interaction between the sample gas and the beam for light absorption, scattering, or subsequent emission to be detected. In some sample cells and analyzer configurations, reflecting the beam within the sample cell along a predetermined path can increase the path of the beam. As discussed in greater detail below, the interior of the sample cell can be modified consistent with implementations of the current subject matter to reduce the amount of gas needed to fill or flush the sample cell.

A radiation beam, such as for example a beam used in spectroscopic analyzers, can have a cross section defined by a shape of the beam in a plane orthogonal to the axis of beam propagation. The beam cross section can have any of a variety of shapes (e.g. circle, oval, trapezoid, rectangle, etc.) and a cross-sectional size, which can be characterized by one or more characteristic dimensions. Examples of characteristic dimensions can include a beam diameter or beam radius, one or more beam widths, etc. As an example, a beam with a circular cross section could have a radius within which 90% (or some other arbitrary fraction) of the total beam intensity is delivered. A commonly used definition for a laser beam diameter (or with in the case of a non-circular beam cross section), in particular for a Gaussian beams, is a distance between two points having a same intensity value that is some defined fraction of the maximum intensity value. For example, a value of $e^{-2}$ (which is equal to 0.135) times the maximum value is sometimes used as an arbitrary definition of an intensity value that defines the "edge" of a beam such that a distance between two points having that intensity is considers a width of the beam. Consistent with some implementations of the current subject matter, a characteristic dimension of a beam can be defined in this manner. Other definitions of a characteristic dimension of a beam are also within the scope of the current subject matter. For example, a characteristic dimension for a beam can include a separation distance for two points between which greater than approximately 99.5% of the beam intensity occurs, between which greater than approximately 99% of the beam intensity occurs, between which greater than approximately 98% of the beam intensity occurs, between which greater than approximately 97% of the beam intensity occurs, between which greater than approximately 95% of the beam intensity occurs, between which greater than approximately 90% of the beam intensity occurs, between which greater than approximately 85% of the beam intensity occurs, etc.

For radiation sources having a peak intensity approximately along an axis of propagation of the beam and a decreasing intensity with distance away from the axis of propagation, one or more characteristic dimensions can be chosen to define a shape and size of a cross-sectional area within which some defined fraction of the beam intensity occurs.

Flow control and sample cell mechanical stability considerations, among other possible factors, can generally lead to conventional sample cells having significant excess gas volumes, and dimensions that are very large when compared to the cross-sectional size of the radiation beam projected through the gas contained within the sample cell. An excess gas volume, as referred to herein, is generally considered to include volume that is at least partially enclosed within one or more walls of a sample cell and that is not within the cross section of a beam path traveling between a radiation source and a detector in a spectroscopic sample cell. For example, conventional cylindrical sample cells used with spectroscopic gas analyzers can typically be many times larger than the cross-sectional size of the beam path. In multi-pass sample cells (an example of which is a Herriott cell) in which spectroscopic sensitivity is improved by increasing the total optical path length that travels through the contained gas volume, a significant excess gas volume of the sample gas contained within the sample cell during any given measurement is not contained within the cross sectional area of any leg of the multiple legs of the beam path.

FIG. 1 shows an example of a multi-pass sample cell 100 that illustrates the above-mentioned effect. A radiation path 102 (referred to in the rest of this disclosure as a beam or laser path for simplicity) passes multiple times through an inner volume 104 of the sample cell 100. The inner volume 104 is at least partially enclosed within outer walls 106 of the sample cell 100. The outer walls 106 can optionally be configured in a cylindrical shape. Other shapes are also possible. At least one mirror 110 (two mirrors are used in the sample cell 100) or other reflective surface causes reflection of the laser beam to result in the multiple passes of the laser beam through the inner volume 104. The beam can enter and exit the inner volume 104 through one or more ports (e.g. one or more holes, pass-throughs, windows, etc.) 112, which can optionally be disposed in a mirror 110. As shown in FIG. 1, a single port 112 can allow the beam to enter the inner volume after generation by a radiation beam source (not shown in FIG. 1) and to exit the inner volume, for example on its way to a detector (also not shown in FIG. 1). Other configurations in which separate ports 112 are provided for entry and exit of the beam 102 are also possible.

As illustrated in the example of FIG. 1, a typical sample cell, including but not limited to a typical multi-pass sample cell, can include a significant excess gas volume 114 through which the beam 102 does not pass. For example, in a sample cell configuration featuring one or more mirrors 110 that have curved or otherwise shaped reflective surfaces, the beam 102 can traverse the distance between the mirrors 110 in a manner that creates excess gas volume 114 near the outer walls 106. A width 120 (e.g. a dimension orthogonal to a centerline 116 of the sample cell 100) of this excess gas volume 114 can increase to a maximum in the vicinity of a midplane 122 between the mirrors 110.

The width 120 of the excess gas volume 114 at any point along the outer wall 106 can be defined as a distance between an inner surface 202 of the outer wall 106 and a characteristic dimension 204 of a cross-sectional size of a closest part of the beam 102 to the inner surface 202. In an example in which the beam has an at least approximately circular cross section, a beam diameter or beam radius can be used as a characteristic dimension 204 of the cross-sectional size of the closest part of the beam to the inner surface 202. For non-circular beam cross sections, a characteristic dimension can be a width of the beam in a direction oriented toward the closest surface feature of the sample cell approached by the beam as it passes through the sample cell. For example, a beam with an oval cross section can be approximately defined by two orthogonal beam widths, which are themselves orthogonal to the axis of beam propagation. Whichever of the two beam widths is oriented toward a sample cell internal surface at a position of closet approach of the beam to the sample cell internal surfaces can be defined as a characteristic dimension.

Figure 2:
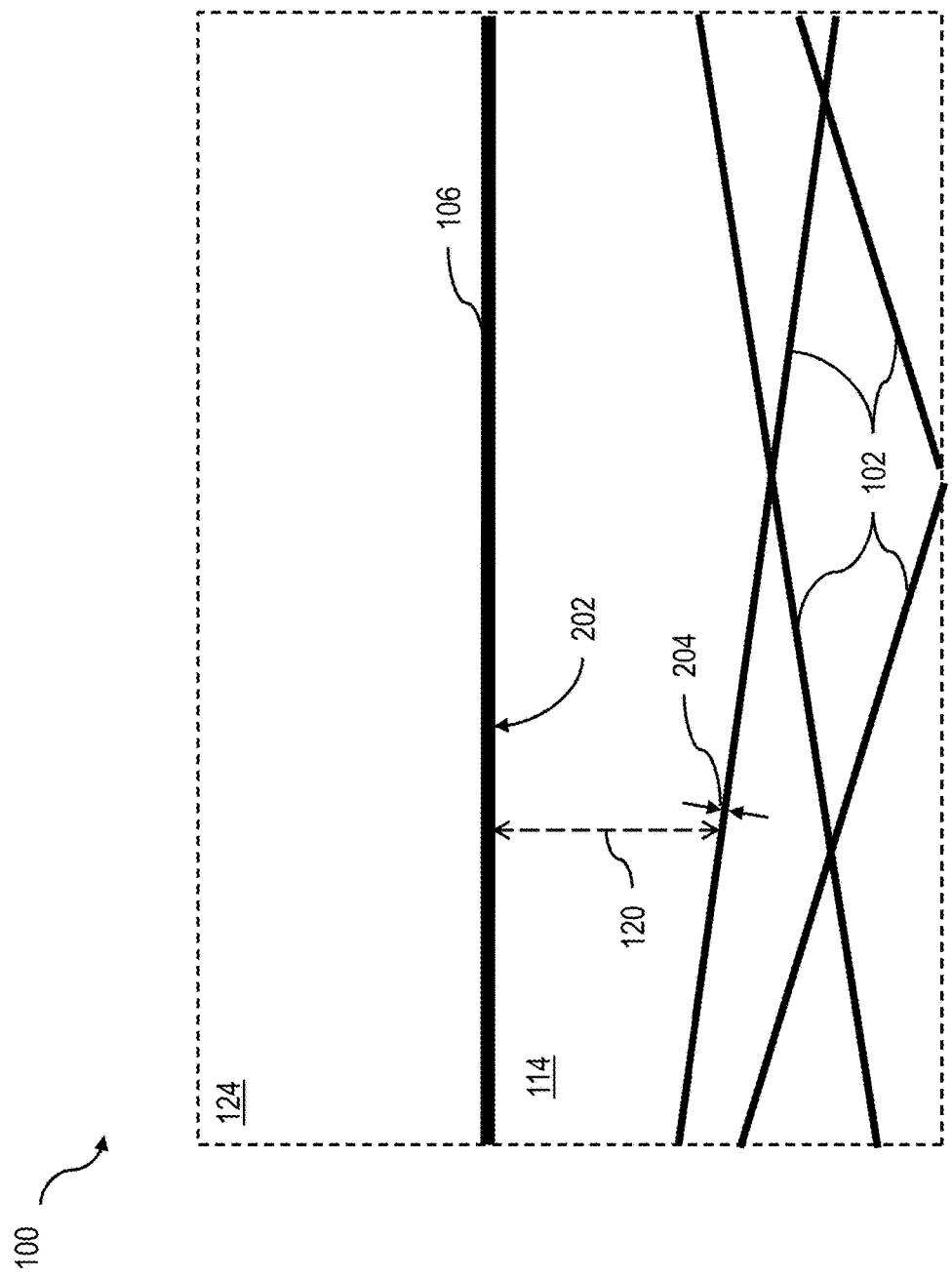
FIG. 2 shows a magnified view illustrating features of the sample cell shown in FIG. 1.

FIG. 2 shows a magnified view of a part of the sample cell 100 of FIG. 1 shown in the dotted rectangle 124. As illustrated in this figure, the shape of the excess gas volume between the inner wall 202 of the outer wall 106 of a cylindrical sample cell 100 can be defined as a solid of rotation having an outer radius equal to an inner radius of the outer wall 106 (e.g. a distance from the inner surface 202 to the centerline 116). The solid of rotation can have a hollow core having an inner volume radius that can optionally vary along the centerline 116 such that the difference between the outer radius of the solid of rotation and the inner volume radius at a point along the centerline 116 can be at least approximately equal to the distance between the inner surface 202 of the outer wall 106 and a characteristic dimension of the closest part of the beam 102 to the inner surface 202 at that point on the centerline 116.

Figure 3:
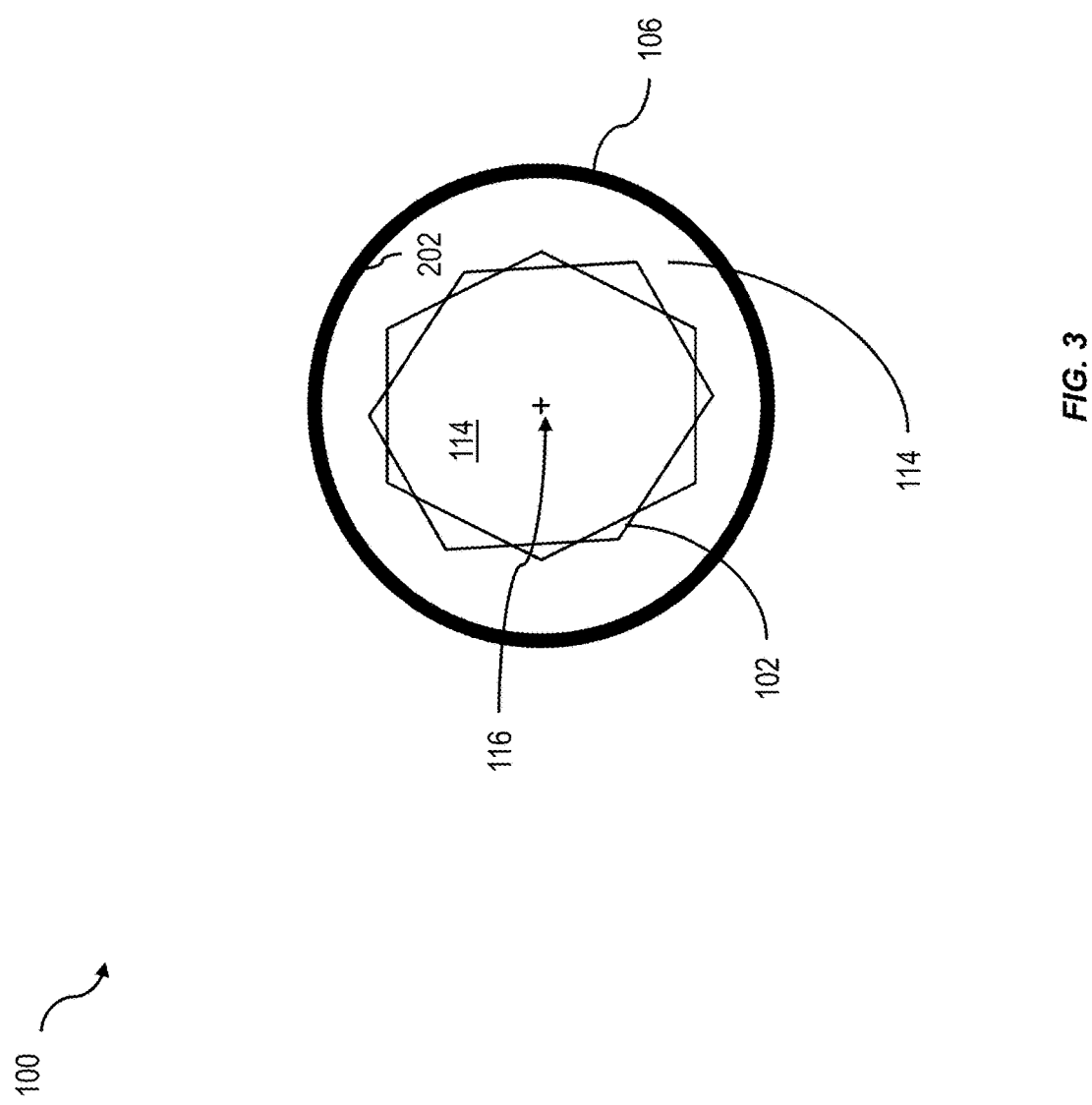
FIG. 3 shows a cross-sectional end view illustrating features of the sample cell shown in FIG. 1.

Further to the discussion of examples of excess gas volumes 114 in a sample cell 100, the excess gas volume 114 can also include part of the sample cell inner volume 104 that is at least partially bounded by two or more parts of the beam 102, but not by the outer wall 106. FIG. 3 shows a cross-sectional view of the example sample cell 100 of FIG. 1 looking along the centerline 116. The beam 102 can be arranged to reflect between the at least one mirror 110 such that the parts of the beam 102 passing between mirrors 110 are directed along vectors having an axial component (e.g.

in a direction parallel to the centerline 116) as well as an axial or circumferential component (e.g. in a direction either moving toward or away from the centerline 116 and/or in a direction consistent with rotation about the centerline 116). The parts of the beam 102 shown in FIG. 3 are intended to illustrate this feature of the beam 102 in that parts of the beam 102, when viewed along the centerline 116, appear to form a woven or otherwise interleaved circumferential pattern as they pass between the mirrors 110. Excess gas volume 114 can be present both inside of this circumferential pattern and outside of this circumferential pattern between the outer contours of the circumferential pattern and the inner surface 202 of the outer wall 106 of the sample cell 100.

Consistent with implementations of the current subject matter, it can be advantageous to reduce the size of the excess gas volume 114 within a sample cell 100. One or more approaches can be applied to achieve such a reduction. Non-limiting examples include shaping an outer wall 106 of the sample cell 100 such that a contour of the outer wall more closely follows a shape of the one or more parts of the beam 102 as it traverses the sample cell inner volume 104 by reflection off of one or more mirrors 110. In other examples, one or more inserts, objects, or the like can be positioned within the inner volume 104 of the sample cell 100 such that at least some of the volume that would otherwise be excess gas volume 114 is occupied and therefore does not contain sample gas. In this manner, a reduced amount of sample gas is required to be present in the sample cell 100 during a spectroscopic analysis. Additionally, for a sample cell 100 used for sequential sampling of a gas stream or other gas volume, one or both of an amount of time at a given gas flow rate or a total volume of gas passing through the sample cell required to reach a new steady state after a change in an inlet concentration of the gas stream can be reduced using features consistent with implementations of the current subject matter.

Figure 4A:
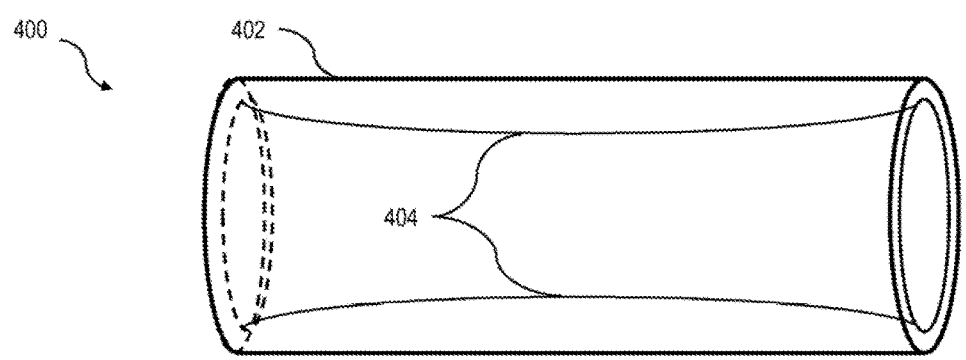
FIG. 4A and FIG. 4B show views of inserts for use with a sample cell consistent with implementations of the current subject matter.
Figure 4B:
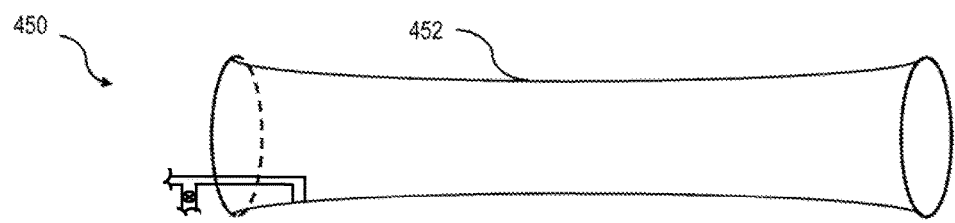

Further with reference to FIG. 1 through FIG. 3, FIG. 4A and FIG. 4B show examples of shaped inserts or objects that can be used to reduce the excess gas volume 114 within a sample cell 100. It will be understood that shaped features, including but not limited to those shown in these drawings and in other drawings filed with this specification, as well as other volume reducing features described herein, can be provided on structurally separate parts of a sample cell assembly, or can be integrally constructed as part of a sample cell. FIG. 4A shows an example of an outer insert 400 and FIG. 4B shows an example of an inner insert 450 that can occupy at least part of an excess gas volume 114 within a sample cell.

Consistent with implementations of the current subject matter, the outer insert 400 can be configured to fit within the inner surface 202 of the outer walls 106 of a sample cell 100. In other words, an outer surface 402 of the outer insert 400 can in some examples be designed to conform to the inner surface 202 of the outer walls 106. In an example in which the outer walls 106 have a cylindrical shape, a radius of the outer surface 402 of the outer insert 400 can be approximately equivalent to (or just slightly smaller within a mechanical tolerance limit than) a radius of the inner surface 202 of the outer walls 106. In an example in which the outer walls 106 define some other shape, the outer surface 402 of the outer insert 400 can conform to a shape of the inner surface 202 of the outer walls 106 of the sample cell 100. Also as noted above, the outer insert 400 can be an integral part of the outer walls 106 (e.g. the outer walls can be constructed, machined, etc. to include features that occupy at least some part of the internal volume 104 of the sample cell that would otherwise become excess gas volume 114 when the sample cell contains a gas and a beam 102 is directed into the inner volume. The outer insert 400 can also have an inner surface 404, which can be shaped such that interference (e.g. blocking) of the beam 102 either does not occur at all or is otherwise has a limited (e.g. an analytically insignificant) effect when the outer insert 400 is positioned within the sample cell 100 and the beam passes through the sample cell along its intended path between a source and a detector. As noted above, some or all of the first insert can optionally be either a separate apparatus that is machined, made, manufactured and then included within the sample cell or, alternatively, an integral feature of the sample cell walls themselves.

Consistent with implementations of the current subject matter, the inner insert 450 can have at least an outer surface 452. In reference to the sample cell 100 and beam 102 shown in FIG. 1 through FIG. 3, an inner insert 450 can be configured to fit within the inner surface 202 of the outer walls 106 of a sample cell 100 such that an annular gap is formed between the inner surface 404 of the outer insert 400 and the outer surface 452 of the inner insert 450. In this manner, an outer insert 400 can be disposed adjacent to the inner surface 202 and an inner insert 450 can be sized and positioned to further reduce the clearance distance in cooperation with the outer insert.

One or more inserts or other structural features, objects, etc. can advantageously be included into a sample cell assembly such that excess gas volume 114 is reduced while also causing no more than an acceptably limited amount of interference with the transmission of radiation along a beam 102 that traverses the sample cell over at least one beam part. As used herein, interference with a beam is considered to not occur or otherwise be acceptably limited if a clearance distance between a closest internal surface of the sample cell is sufficient to avoid such interference. For example, a clearance distance can be defined as a multiple of a characteristic dimension of the cross-sectional size of the beam, and this clearance distance can exist at least at a location of closest approach between a part of the beam 102 and an internal surface of the sample cell. Internal surfaces of the sample cell can include walls and/or other features (e.g. gas-exposed surfaces of inserts, etc.) that contact the gas within the sample cell.

Figure 5:
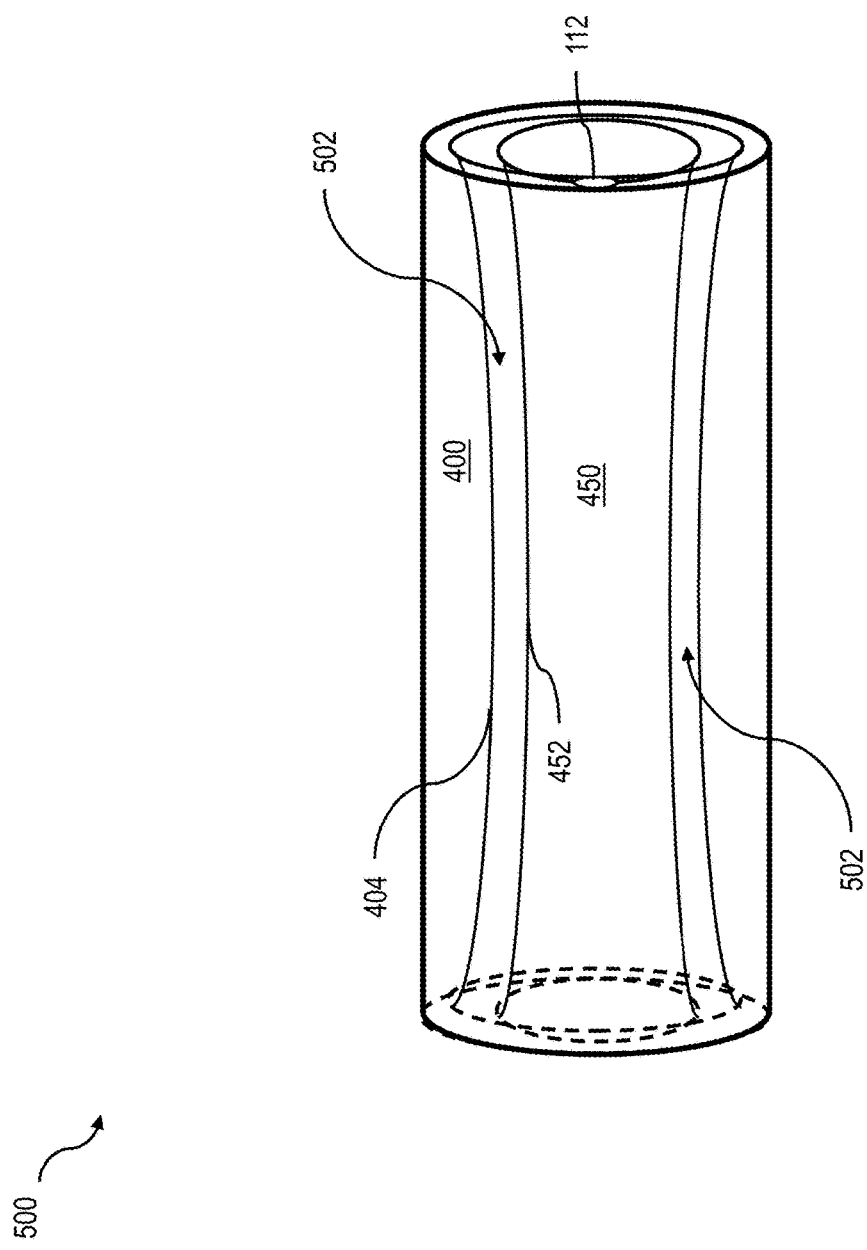
FIG. 5 shows an isometric diagram illustrating a sample cell assembly consistent with implementations of the current subject matter.

FIG. 5 shows a sample cell assembly 500 consistent with implementations of the current subject matter. In this example, the sample cell outer walls 106 encircle both of an outer insert 400 and an inner insert 450 such that an annular gas volume 502 remains open for passage of multiple parts of a beam 102 (not shown in FIG. 5). The port or ports 112 through which the beam enters the annular gas volume 502 can be positioned such that passage of the beam through the port or ports 112 is not impeded or interfered with by either of the outer insert 400 or the inner insert 450. It will be readily understood that a sample cell configuration including features resembling either or both of an outer insert 400 or an inner insert 450 as discussed above can In some implementations of the current subject matter, an insert can include one or more reflective surfaces or mirrors that can allow the insert to reflect the beam as the beam passes through a gas volume that is constrained by a surface of the insert. For example, in the sample cell assembly 500 of FIG. 5, at least part of either or both of the inner surface 404 of the outer insert 400 and the outer surface 452 of the inner insert 450 can be reflective such that a part of the beam passing through the annular gas volume 502 is reflected one or more times off of either or both surface. In still other implementations of the current subject matter, a feature similar to the outer insert 400 can include an inner surface 404 having at least some reflective area, and the inner insert 450 can be omitted such that the beam is reflected multiple times through a gas volume 114 constrained by the inner surface 404 of the outer insert 400 and the one or more mirrors 110 at the ends of the sample cell assembly 500.

A sample cell assembly 500 can alternatively include a feature similar to the inner insert 450, optionally with or without at least some of the outer surface 452 of the inner insert 450 having reflective features. In such configurations, the inner surface 202 of the outer wall 106 of the sample cell can optionally include some reflective area, or alternatively, the beam can reflect only from the mirror 110 (or mirrors) and optionally the outer surface 452 of the inner insert 450.

Parameters that can be used in determining an advantageous shape of an inner surface 404 of the outer insert 400 and/or the outer surface of an inner insert 450 are discussed in greater detail below. It will be understood that a sample cell assembly incorporating features of either or both of an outer insert 400 and an inner insert 450 is consistent with one or more implementations of the current subject matter. Additionally, sample cell shapes and configurations other than cylindrical are also within the scope of the current subject matter.

Consistent with the descriptions of example implementations provided herein, sample cells and sample cell assemblies and methods of manufacture and use consistent with the current subject matter enable minimization of the excess gas volume in a sample cell of a spectroscopic analyzer. In some implementations, a maximum clearance distance between a surface of the sample cell walls or surface of an insert that occupies volume inside the sample cell can be defined as a multiple of a characteristic dimension of the beam. In other words, in an analyzer in which a beam passes one or more times through a sample cell, the contours of the inner surfaces of the sample cell, and optionally of one or more inserts that occupy some part of an excess gas volume defined by the inner surfaces of the sample cell, can be configured such that a clearance distance between at least one closest part of the beam and at least one closest solid surface to the beam is less than the defined maximum clearance distance.

In some examples, a maximum clearance distance between a center of a part of the beam and a solid surface bounding the inner volume 104 in the sample cell can advantageously be less than approximately 35 times the characteristic dimension of the beam (which is defined above). As a merely illustrative example, a circular beam with a characteristic dimension (e.g. a beam diameter) of 100 μm and a maximum clearance distance defined as 20 times the characteristic dimension can have a clearance distance between at least one closest part of the beam and at least one closest solid surface to the beam of approximately 2 mm or less from the beam center at the closest approach of a part of the beam to that solid surface.

Typical beam characteristic dimensions can depend upon a reflector radius of curvature, a distance between one or more mirrors or other reflectors, etc. such that a characteristic dimension beam dimension can be substantially smaller than 100 μm, or alternatively in a range of approximately 700 to 1500 μm. Other beam characteristic dimensions are also possible. For example, a beam used in Raman spectroscopy can have a characteristic dimension as small as approximately 0.4 μm. A characteristic dimension of a beam may also not be constant with distance along a axis of propagation of the beam. For example, a characteristic dimension such as a beam diameter might vary as a function of proximity to a reflection point. In one example, a beam diameter can be approximately 300 μm near a focal point of the beam and approximately 1000 μm on or near a mirror.

In other implementations of the current subject matter, the maximum clearance distance can be defined to be in a range of approximately 1 to 100 times the beam characteristic dimension. Alternatively, the maximum clearance distance can be defined to be in a range of approximately 1 to 75, in a range of approximately 3 to 75, in a range of approximately 1 to 50, in a range of approximately 3 to 50, in a range of approximately 1 to 35, in a range of approximately 3 to 35, in a range of approximately 1 to 20, in a range of approximately 3 to 20, in a range of approximately 1 to 10, or in a range of approximately 3 to 10 times the beam characteristic dimension. In other examples, the maximum clearance distance can be approximately 1, 2, 3, 4, 5, 6, 7, 8, 9, 10, 12, 14, 16, 18, 20, 25, 30, 40, 50, 60, 65, 75, etc. times the beam characteristic dimension. In this manner, the excess gas volume contained within a sample cell can be reduced and advantageously minimized, such that an analyzer incorporating such a sample cell can more rapidly respond to a change in concentration of one or more analyte compounds (or to a varying background composition) in a sampled gas volume or gas stream. Exchange of gas through which the beam passes can be substantially accelerated without sacrificing absorption path length in the sample cell.

Other, previously available sample cell configurations have included Herriott cells and other multi-pass sample cells having spherical or aspherical mirrors 110 at one or both ends of a cylindrical sample cell body (e.g. one defined by the outer walls 106 as shown in FIG. 1). In a typical sample cell configuration employing opposed spherical mirrors, the parts of the beam are reflected between reflection points that are arranged in a circle or elliptical pattern on each of the two mirrors. Sample cell configurations using aspherical or astigmatic mirrors can typically achieve longer absorption path lengths then a cell of comparable size (thereby reducing the gas volume within the sample cell), for example by routing the reflected beam to reflection points located elsewhere besides on the circle pattern typical of spherical mirrors, which allows a larger number of reflections between the mirrors to create a longer path-length for a given distance between the mirrors. In this manner, the sample cell volume is reduced. As an example, cavity ring-down spectroscopy (CRDS), integrated cavity output spectroscopy (ICOS), and other spectroscopic approaches that use astigmatic cavities typically fold long absorption path lengths into small tube diameters by utilizing not just a location of reflective spots disposed about a circle close to the inner diameter of the confinement walls of a sample cell, but also the reflective area within such this circle of laser reflection spots which would be typical for a Herriott cell configuration. Such an approach can have the disadvantage of increased beam intensity losses due to an increase in less than ideal reflections. For example, two mirrors that are each 98% reflective would attenuate the intensity of a beam reflected between them by about one third after 20 reflections and by more than half after 35 reflections. Implementations of the current subject matter can advantageously reduce a sample volume and also provide additional improvements in flushing time in excess of those expected simply by reduced gas volume within the cell in a manner than does not require increasing a number of reflections to achieve a same path length.

Additionally, in the case of ICOS, the sample cell is an off-axis optical resonator, which only delivers an absorption signal as long as the resonator is on resonance with the scanning laser frequency. Without complicated and expensive resonator length stabilization servos, there will be no continuous measurement signal obtained from the sample cell. In practicality, the measurement output becomes noisy (especially in comparison to a Herriott cell) when the ICOS resonator is not temperature stabilized. Furthermore, the off-axis resonator can be extremely sensitive to contamination of the mirrors, which can result in a shortened useful life-time of such cells or extra precautions that must be taken to avoid contaminating the mirrors, in particular in process flow measurements, petrochemical or natural gas pipelines, or similar analytical environments in which chemical contamination of the mirrors is likely. For example, the actual usable path length and measurement ability of an ICOS can be limited by contamination build up on the mirrors. Mirror losses exceeding ~100 ppm losses can render these techniques completely useless. Neither CRDS nor ICOS work robustly and reliably, in a hands-off manner, in typical natural gas and process petrochemical absorption measurement applications.

Sample cells with astigmatic reflectors can in some examples be less robust against mechanical bending and environmental changes than typical Herriott cells using spherical mirrors. However, consistent with implementations of the current subject matter, excess gas volume within the sample cell can be occupied by contouring outer walls of such sample cells and/or by inclusion of one or more inserts. A maximum clearance distance consistent with other explanations herein can be used in such sample cells as well.

In some implementations of the current subject matter, an inner insert 450 can be solid or hollow. Optionally, at least some of the volume occupied by the inner insert can house other analyzer system components, such as for example electronics components, wiring components, scrubber, one or more scrubber components, flow control components (e.g. tubing, valves, etc.), or the like, which can reduce a total size of the spectroscopic system. In other words, an insert can include a component volume that is isolated from the gas volume and configured to house one or more components of a spectroscopy system. Size considerations for gas analyzers can be important in some situations, for example for analysis systems designed for deployment in industrial or remote settings. As spectroscopic analysis of gas compositions can be sensitive to temperature and other environmental factors, reduction in the size of the components of an analysis system can lead to reductions in energy usage by the analyzer, as a smaller environmentally controlled enclosure can be used than would otherwise be necessary.

In some implementations, a sample cell can include features of an optical resonator, in which the beam travels back and forth between two reflectors, inside a tubular or slab configuration. In such implementations, the path of the laser beam can be optimized within the modified configuration of the enclosure, for example as in a modified tubular or prism enclosure. Additionally, or alternatively, the modifications to the interior of the sample cell can be optimized to allow for maximal path length when the path of the laser beam is predetermined.

Herriott cell, White cell, and other sample cell configurations for beam measurements that use at least one spherical reflector and one reflector of arbitrary shape (e.g. a flat reflector) can benefit from shaping the outer sample cell wall along the beam path to contour the propagation shape envelope of the reflected beams. The alteration of the outer wall of the sample cell can be such that the distance between the laser beams and the sample cell enclosure wall is less than the maximum clearance distance as discussed above. In addition, a second insert shaped to follow the inner contour of a reflected beam envelope to within such a maximum clearance distance can occupy a center area of such a cell configuration. In a typical Herriott cell, an approach as described herein can result in a hyperbolically shaped annular-shaped flow configuration that encapsulates the propagating laser beams and guides the flow of the gas to be tested.

In other implementations of the current subject matter, a sample cell can include an enclosure (e.g. a tubular enclosure) through which the beam travels in one direction. In other words, the beam enters the enclosure through different ports located oppositely along some travel distance within the enclosure of the sample cell. A laser or other radiation source can be located at one end of the enclosure to direct a beam of radiation into the enclosure, and a detector can be located at another end of the enclosure to receive the beam and quantify a received intensity for use in quantifying absorption of the beam by gas in the enclosure. This sample cell implementation can include reflective walls or boundaries of the enclosure such that the beam is reflected within the enclosure to provide a path length that is longer than the linear dimension of the enclosure. For a tubular enclosure, the inner diameter of the enclosure can advantageously be less than 20 times a radius of the laser beam. The maximum clearance distance within a tubular enclosure can optionally be constrained by the same parameters discussed above for a multi-pass sample cell. The length of a tubular enclosure can in one example be at least 0.01 mm.

Figure 6:
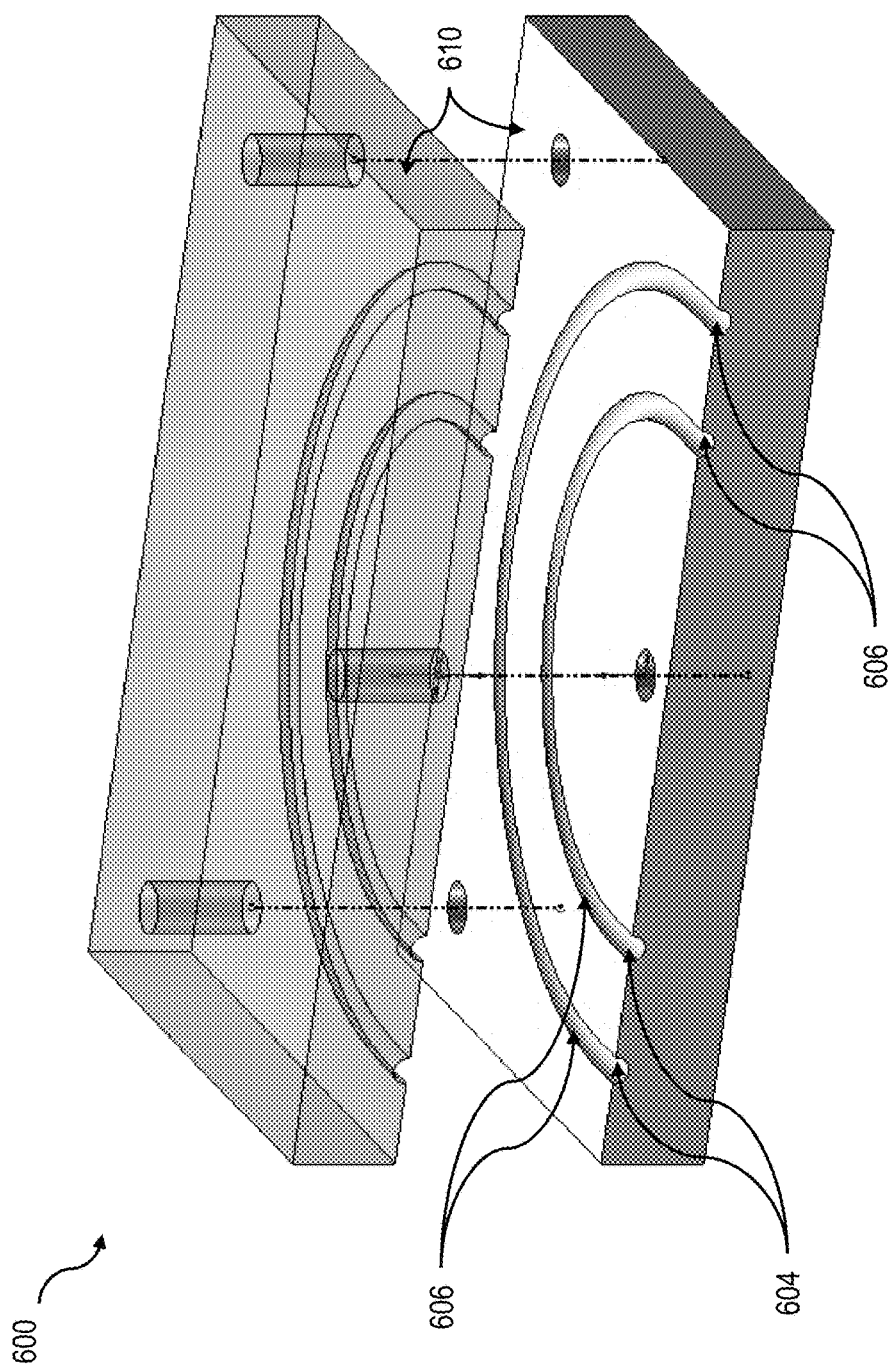
FIG. 6 shows an isometric diagram illustrating another sample cell assembly consistent with implementations of the current subject matter.

In an alternative implementation, a sample cell can be a shape other than rotationally symmetric. At least one dimension perpendicular to the direction of travel of the laser beam can be less than 50 times the beam radius at any location along the path of the laser beam. Such a sample cell configuration includes but is not limited to a hollow slab made from two flat plates such as the example sample cell sample cell 600 shown in FIG. 6. This sample cell 600 can have one or more features in common with an optical resonator. A beam (not shown in FIG. 6) enters a channel 602 at one end 604 and exits the channel 602 at a second end 606. In FIG. 6, two channels 602 of differing length are shown. A channel 602 can receive the beam from a radiation source (not shown in FIG. 6) directed toward the first end 604 and deliver the beam to a detector (not shown in FIG. 6) positioned at the second end 606. The channel can be curved to fit into a round plate, which can in some implementations be manufactured from two mating halves of a metal block 610 or the like with corresponding machined grooves. The block 610 can be made of other materials besides a metal, such as for example ceramic, composites, glass, semiconductor materials, plastics, or the like. Some or all of the internal surfaces of the channel can optionally be polished, coated, or otherwise treated to increase reflectivity of the beam as it traverses the channel by one or more reflections off of the internal surfaces. A gas path (not shown in FIG. 6) can be provided through the block 610. For example, a gas inlet path and a gas outlet path can be provided from above or below the channel (e.g. perpendicular to the beam path in a channel 602).

Implementations of the current subject matter can achieve an unexpected improvement in the time required for gas within a sample cell to equilibrate to a second gas composition from a first gas composition upon a change in an inlet concentration of gas flowing through the sample cell. Various idealized flow models can be used to predict concentration changes within a sample cell based on a change in input concentration of a gas stream passing through the sample cell. It will be understood, however, that an idealized flow model may not fully represent the flow conditions within a non-ideal sample cell.

A plug flow reactor (PFR, also referred to as a piston flow reactor or a continuous tubular reactor) model can be applied to predict flow in a continuous flowing system in which mixing along an axis of flow is assumed to be negligible. Another reactor model is the continuous flow stirred tank reactor (CFSTR) in which the contents of a sample cell are assumed to be perfectly and instantaneously mixed such that flow out of the sample cell occurs at the current concentration within the chamber. Equations expressing the concentration of an analyte measurable by a beam of radiation traversing the sample cell as a function of time after a change in an inlet concentration can be derived based on the analysis discussed in the following paragraphs.

For a PFR model of a sample cell, the sample cell is assumed to have a length L along a direction of flow with an inlet at a distance 0 and an outlet at a distance L from the inlet. At a start time ($t_0$), the concentration is assumed to be constant along the distance L at an initial concentration $C_0$. Also at $t_0$, the inlet concentration is changed to a new concentration $C_1$. Because the gas flowing through a PFR-modeled sample cell is assumed to be experience no mixing along the direction of flow, the change in inlet concentration from $C_0$ to $C_1$ results in a "plug" of the new concentration moving through the sample cell from distance 0 to L at an average flow velocity $v_{flow}$. The average flow velocity $v_{flow}$ in such a system is the volumetric flow rate Q divided by the cross sectional area A of the sample cell orthogonal to the direction of flow. In other words, the time $t_{equil}$ for the sample cell to equilibrate from $C_0$ to $C_1$ under an assumption of plug flow can be estimated as follows:

$$t_{equil} = L/v_{flow} = L \cdot A/v_{flow} \cdot A = V/Q \quad (1)$$

In other words, a PFR model for a sample cell provides a "best case" value for the time required to fully replace a first gas composition in a sample cell with a second gas composition. For perfectly plug flow conditions, flow of a volume of gas equal to the sample cell volume through the sample cell is sufficient to replace the first composition with the second composition.

For a CFSTR model of a sample cell, it can also be assumed that the sample cell has a length L and a cross sectional area A such that the volume V of the cell is the product of L and A. As with the PFR model, the flow rate of gas entering the sample cell is Q. Unlike the PFR model, however, the concentration at the outflow in the CFSTR model changes in relation to the changing concentration within the volume V=L·A of the sample cell. As with the PFR model discussed above, in the CFSTR model example, the initial concentration $C_0$ is present in the sample cell at a start time ($t_0$). Also at $t_0$, the inlet concentration is changed to a new concentration $C_1$. In such a reactor model, the following differential equation describes the change in amount of the analyte in the sample cell with time:

$$\frac{dCV}{dt} = -QC_1 - QC(t) \quad (2)$$

A characteristic time $\tau$ for a CFSTR-modeled sample cell is generally defined as the volume of the sample cell V divided by the volumetric flow rate Q through the sample cell Q. Solving equation 2 for the sample cell concentration as a function of time C(t) and substituting $\tau$ for the ratio of V/Q yields the following relationship:

$$C(t) = C_1 - (C_1 - C_0) \cdot e^{-t/\tau} \quad (3)$$

Equation 3 is an exponential decay equation with time constant $\tau$. Accordingly, $\tau$ can also be considered to be the mean lifetime of the sample cell, in other words, the average period of time that any specific molecule remains in the sample cell. After 3 mean lifetimes, an exponential decay equation approaches 95% of the steady state value, and after 4 mean lifetimes, an exponential decay equation exceeds 98% of the steady state value. A CFSTR model therefore provides a less optimal speed of gas replacement in a sample cell. As many as four sample cell volumes may need to be exchanged through the sample cell to achieve an effective replacement of a first composition with a second composition.

Thus, in a sample cell that is perfectly modeled as a PFR, the time to reach the new concentration is $t_{equil}$=V/Q while in a CFSTR, a 98%+ equilibration to the new concentration takes at least 4·$\tau$ or 4·V/Q. Application of theories of fluid flow mechanics can indicate that laminar flow through a tube or the like may not be accurately modeled as a PFR, at least because of boundary layers effects, etc. that cause fluid nearer to a stationary surface to move more slowly while fluid further from that surface tends to have a higher velocity. In a cylindrical flow regime, such as for example some of the sample cells discussed above, a laminar flow profile through the sample cell might have a parabolic pattern of fluid velocities with the highest velocities (e.g. higher than the average flow velocity $v_{flow}$) closest to the central axis and the slowest velocities (e.g. lower than $v_{flow}$) closest to the side walls. Thus, for a given volumetric flow rate, the time to achieve a full exchange of the gas originally in the sample cell to a new inlet gas stream concentration might be expected to be longer than $t_{equil}$=V/Q. To the extent that significant mixing occurs along the direction of flow for any reason, this can also cause the time to achieve a full exchange of the gas originally in the sample cell to a new inlet gas stream concentration to exceed $t_{equil}$=V/Q.

Figure 7:
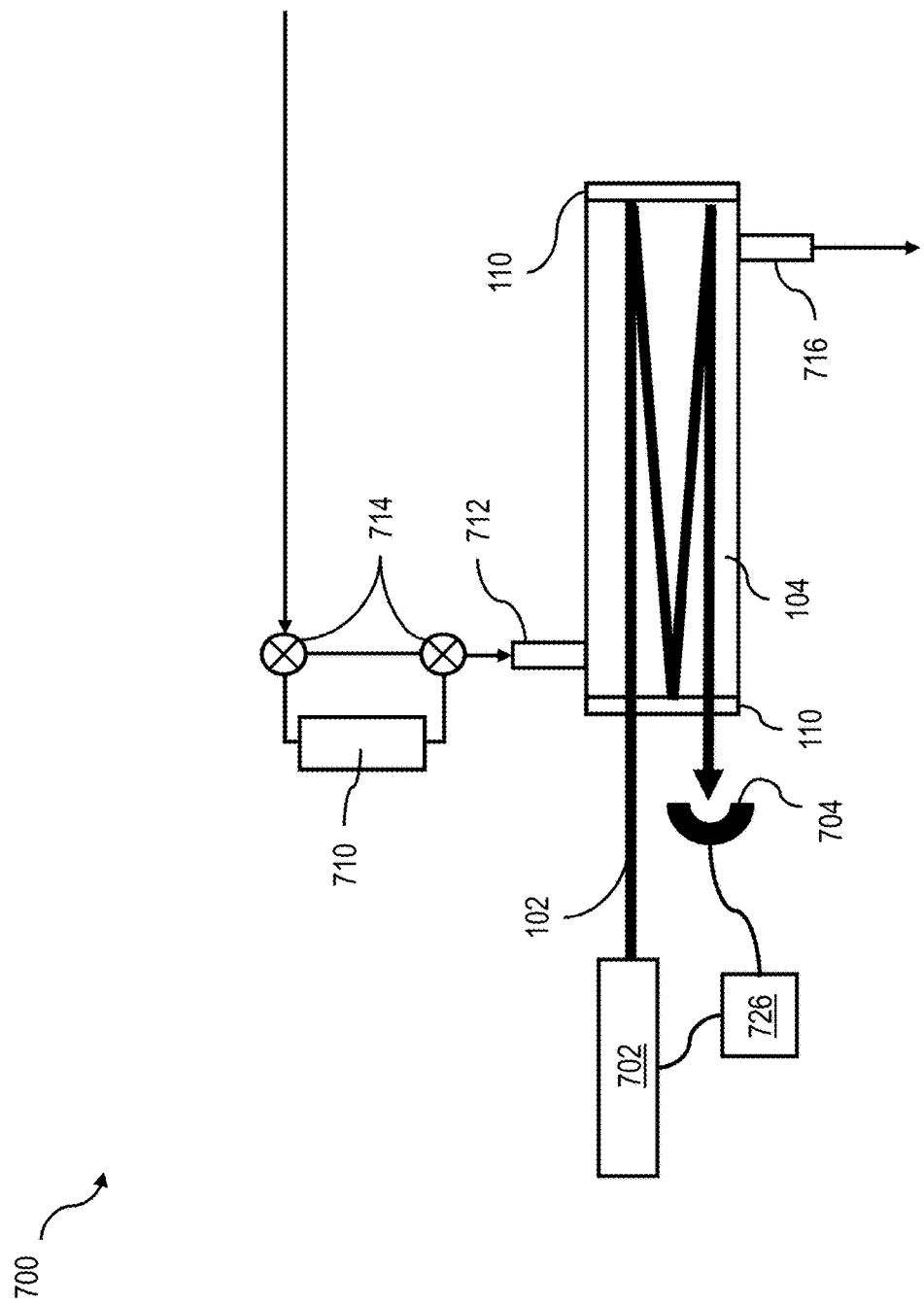
FIG. 7 shows a spectrometer system consistent with implementations of the current subject matter.

As a demonstration of one or more benefits achievable using implementations of the current subject matter, a 28 m path length Herriott cell having an internal volume of approximately 1260 mL was tested by switching an inlet gas stream having a first concentration of an analyte (in this example, hydrogen sulfide) to a gas containing a zero concentration of the analyte. A spectroscopic analyzer incorporating the Herriott cell was used to monitor the analyte concentration in the Herriott cell as a function of time after the switching of the inlet gas stream. FIG. 7 shows a schematic diagram of a spectrometer system 700 similar that can be useful in understanding the described test. As shown in FIG. 7, a beam 102 from a radiation source 702 (e.g. a laser or the like) is directed through a sample cell 100 and reflected between two mirrors 110 through the sample cell 100 before exiting the sample cell and reaching a detector 704. A controller 706 controls operation of the laser 702 and receives and analyzes signals from the detector 704 to determine analyte concentrations in the sample gas in the sample cell 100.

The beam reflection pattern shown in FIG. 7 is not intended to be representative of any specific or actual beam reflection pattern but merely represents a simplified depiction of a reflected beam having multiple reflected parts. The test gas delivered to the internal volume 104 of the sample cell can either pass through or bypass a scrubber 710 (e.g. the scrubber 710 can be placed in series with a gas inlet 712 to the sample cell 100 by operation of one or more valves 714). The scrubber 710 removes hydrogen sulfide from inlet gas stream passing through it while generally leaving other components of the test gas unaffected. Gas flows out of the sample cell 100 via a gas outlet 716. Use of the scrubber 710 allows a stepwise change in the inlet concentration provided to the sample cell 100 from an initial, known concentration to a zero concentration. The concentration of hydrogen sulfide was measured using the laser 702 and detector 704 as controlled by the controller 706. After switching of the valves 714 to direct the test gas through the scrubber 710 (and thereby reduced the hydrogen sulfide concentration to effectively zero), the hydrogen sulfide concentration in the sample cell 100 was monitored as a function of time.

With an inlet gas stream flow rate of approximately 3 L·min$^{-1}$ (liters per minute), the hydrogen sulfide concentration in the sample cell 100 drops below detection limits of the spectroscopic analyzer within about 45 seconds after switching to the scrubbed inlet gas. As the PFR equilibration time for the sample cell in this configuration is approximately 25.2 seconds (1.260 L volume÷3 L·min$^{-1}$ flow rate× 60 seconds per minute), the time to equilibrate to the new concentration was more than 2·τ. Flushing of the sample cell clearly does not proceed according to an idealized PFR model and is perhaps better represented as a CFSTR.

In a second test with the same Herriot cell under comparable flow conditions, the Herriott cell internal volume was modified by the inclusion of a trapezoidal shaped outer insert 400 that occupied some of the excess gas volume outside of the beam envelope and a cylindrical shaped inner insert 450 that occupied at least some of the excess gas volume inside the beam envelope. The term "beam envelope" as used herein refers to an imaginary surface formed by joining the parts of a beam as it reflects within the sample cell. Using these outer and inner inserts, the total gas volume in the Herriott cell was reduced to approximately 570 mL In a test of this modified sample cell, a gas with a known hydrogen sulfide concentration was again passed through the sample cell, this time at only 1 L·min$^{-1}$. Upon switching the valves 714 to direct the test gas through the scrubber 710 (and thereby reduced the hydrogen sulfide concentration to effectively zero), the hydrogen sulfide concentration in the sample cell 100 was monitored as a function of time. In this case, only approximately 36 seconds were required for the hydrogen sulfide concentration in the sample cell to drop below detection limits of the spectroscopic analyzer. The PFR equilibration time for the sample cell in this configuration is approximately 34.2 seconds (0.570 L volume÷1 L·min$^{-1}$ flow rate×60 seconds per minute). In other words, the time to equilibrate to the new concentration was much closer to τ, which indicates a much closer conformance of the sample cell to PFR-modeled performance. Using a flow rate of approximately 3 L·min$^{-1}$ in another test, on the order of approximately 10 to 11 seconds are required for the hydrogen sulfide concentration in the sample cell to drop below detection limits of the spectroscopic analyzer. Under these conditions, the PFR equilibration time is on the order of approximately 11.4 seconds (0.570 L volume÷3 L·min$^{-1}$ flow rate×60 seconds per minute). In other words, within the measurement accuracy at the relatively high flow rates through the sample cell, the equilibration time is roughly equivalent to the PFR-modeled performance. Additional improvements in equilibration times may be achieved via the use of inner and outer inserts that more closely contour to the shape of the beam envelope.

The described modifications to a Herriott cell or other multi-pass sample cell in which a beam reflects to make two or more passes through the length of a sample cell can result in an annular flow environment with at least one curved surface to approximate an inner and/or an outer surface of the beam path envelope. The annular flow environment can be visualized as a volume formed by selection of a shape (e.g. a hyperbolic curve in some examples) that at least partially confirms to some part of the outer beam path envelope that would otherwise be adjacent to an excess gas volume through which no beam part passes and rotation of that shape about a center axis of the sample cell with a central volume omitted. The shape of the center volume in the experimental example discussed above was a simple cylinder chosen to have a diameter slightly smaller (e.g. within a maximum clearance distance) than a narrowest size of the inner beam envelope. Other shapes of an inner insert can more closely contour to the inner surface of a beam envelope. Such modifications do not require a change to the radius of curvature of any mirrors in the system nor any spacing of the mirrors or other components relative to the sample cell configuration without the inserts.

As noted above, the shaping of the volume occupied by the sample gas in a sample cell consistent with implementations of the current subject matter demonstrably improves the gas exchange performance of a sample cell in that equilibration items that are much closer to those expected for an ideal plug flow reactor can be achieved. In this manner, a latency time (e.g. time during which an accurate measurement is not possible) between samples when a composition of the sample gas changes can be improved. Alternatively or in addition, an amount of sample gas (e.g. a gas stream flow rate) required to achieve suitable operating parameters for analysis of a sample gas with a changed composition can be decreased. These changes in operational performance can lead to significant benefits in the application of laser analyzers, such as tunable diode laser analyzers, in the control of natural gas pipelines, due to reducing fugitive greenhouse gas emissions and the time when the analyzer does not actively measure an analyte concentration.

Further to the discussions above regarding potential benefits of turbulent flow, the relative magnitude of turbulent energy in a flowing fluid can be compared across different fluid flow situations using the Reynolds number, which is a dimensionless quantity generally defined as a ratio of inertial forces to viscous forces that quantifies the relative importance of these forces on the fluid flow behavior. An example of a Reynolds number is a ratio of the product of a flow velocity $v_{flow}$ and a characteristic length $L_c$ divided by a kinematic viscosity $v_k$ of the fluid. The kinematic viscosity $v_k$ is itself a ratio of the dynamic viscosity μ of the fluid to the fluid density (ρ). Thus, the Reynolds number Re for a given flow system (e.g. a sample cell as discussed herein) can be calculated as follows:

$$Re = \frac{v_{flow} \cdot L_c}{v_k} \qquad (4)$$

The characteristic length $L_c$ for fluid flowing in a pipe or other physically constrained flow volume can be defined as the hydraulic diameter, $d_H$. The hydraulic diameter, which is commonly used to calculate pressure drop and Reynolds numbers in such flow regimes, is defined as the cross sectional surface area divided by the wetted circumference. For a circular tube $d_H$ is simply the diameter (e.g. two times the radius of the tube). Other equations are applicable more complicated flow geometries. For example, pipe or conduit with a rectangular cross section having sides of length a and b, $d_H$ can be represented as follows:

$$d_H = 2\frac{a \cdot b}{a+b} \quad (5)$$

For a pipe or conduit with an annular cross section, characterized by an inner diameter $r_i$ of an outer ring bounding the cross section and an outer diameter $r_o$ of the inner ring bounding the cross section, $d_H$ can be represented as follows:

$$d_H = 2(r_i - r_o) \quad (6)$$

The kinematic viscosity is a function of the composition of the gas stream as well as temperature and pressure (which together impact density of the gas). As an example, at 20° C. and approximately atmospheric pressure, the kinematic viscosity $v_k$ of both air and methane (a reasonable proxy for many natural gas mixtures) is about $1.5 \times 10^{-5}$ m$^2 \cdot$s$^{-1}$.

Based on the experiments discussed above, a Reynolds number Re can be estimated using a characteristic length as the smallest width of an air passage within the sample cell. For a cylindrical rod inner insert 450 and a trapezoidal shaped outer insert 400, the characteristic length $L_c$ can be the annular distance between the two inserts, for example using $d_H$ as calculated using equation 6 with $r_i$ being the inner radius of the outer insert 400 and $r_j$ being the outer radius of the inner insert 450. In this example, the characteristic length $L_c$ for a sample cell with an annular cross section having $r_i$=0.0209 m and $r_o$=0.0127 m is approximately 0.0165 m. The flow velocity $v_{flow}$ in this system is the volumetric flow rate Q divided by the available cross-sectional flow area at the narrowest point or points of approach of opposing walls of the sample cell flow volume. In this example, for a 1 L·min$^{-1}$ volumetric flow rate Q, the flow velocity $v_{flow}$), is approximately 0.0191 m·s$^{-1}$. For a gas having a kinematic viscosity $v_k$ of $1.5 \times 10^{-5}$ m$^2 \cdot$s$^{-1}$, the Reynolds number Re for the modified sample cell is approximately 20.9.

In contrast, for the unmodified sample cell with a 3 L·min$^{-1}$ volumetric flow rate Q, the flow velocity$_{vflow}$ is approximately 0.0158 m·s$^{-1}$. The characteristic length $L_c$ of the unmodified sample cell would be considered to be the sample cell diameter, which in this example is approximately 0.0254 m, thereby giving a Reynolds number Re of approximately 66 for the unmodified sample cell. In other words, the Reynolds number for the unmodified sample cell at a volumetric flow rate of approximately 3 L·min$^{-1}$ is actually slightly larger than that of the modified sample cell at a volumetric flow rate of approximately 1 L·min$^{-1}$, and the Reynolds numbers in both cases are significantly lower than the threshold value of 2300 typically assumed to indicate the presence of predominantly turbulent flow.

Figure 8:
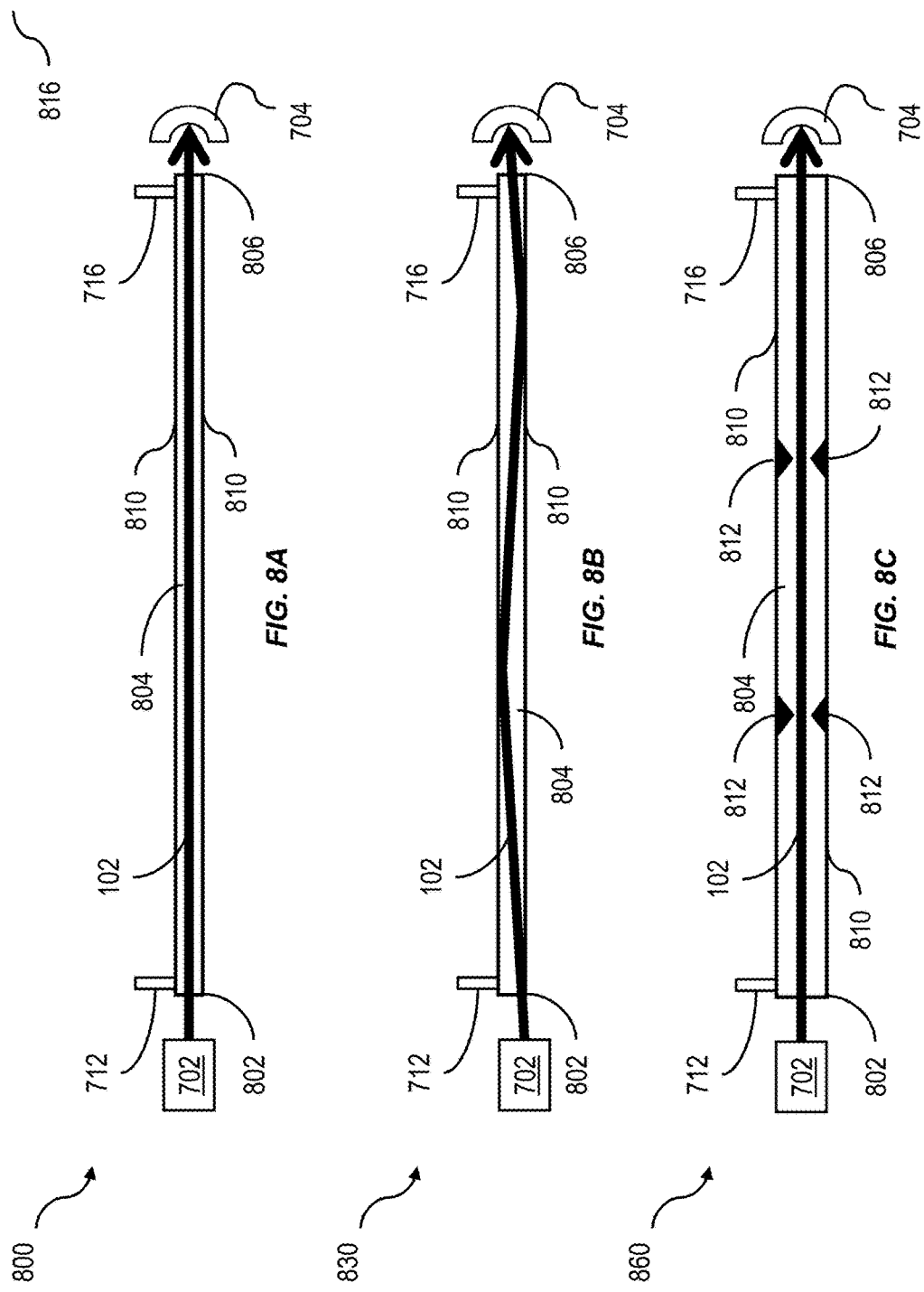
FIG. 8A, FIG. 8B, and FIG. 8C show other sample cell configurations consistent with implementations of the current subject matter.

Improved sample gas equilibration performance is also expected in sample cells other than a multi-pass sample cell such as that used in the experiments discussed above. For example, a sample cell consistent with implementations of the current subject matter can be realized as a gas passageway, which can optionally be either a straight tube or a tube having one or more bends (e.g. as in the example of FIG. 6). Such a tube can be circular in cross section or can have some other cross-sectional shape (e.g. rectangular, square, oval, elliptical, etc.). A gas inlet and a gas exit can be connected to the tubular sample cell proximate to the opposing ends of the tubular shape to enable gas flow. FIG. 8A, FIG. 8B, and FIG. 8C show schematic diagrams illustrating several features of sample cells consistent with implementations of the current subject matter.

As shown in the system 800 of FIG. 8A, a beam can propagate from a source 702, which can be positioned at a first end 802 of a gas passageway 804, to a detector 704, which can be positioned at a second end 806 of the gas passageway 804. Alternatively, a gas passageway 804 can feature a reflector at one or more ends of the tubular shape such that a beam in the gas passageway 804 is reflected at least once. In such an example, the source 702 and the detector 704 can optionally be at a same end of the tubular enclosure or at opposite ends. The gas passageway 804 can optionally have a maximum clearance distance between opposing internal surfaces (e.g. between opposing walls 810) such that the maximum clearance distance in at least one dimension, which can optionally be at least approximately perpendicular to the axis of propagation of the beam as shown in FIG. 8A, is less than some multiple (e.g. less than 20 times, less than 10 times, less than 5 times, etc.) of a characteristic dimension of the beam. While the beam 102 in FIG. 8A is shown oriented at least approximately along a center axis of the gas passageway 804, this depiction is not intended to be limiting. A beam 102 can optionally be arranged more closely to one or more internal surfaces of a sample cell than to one or more other internal surfaces of the gas passageway 804. The axis of propagation of the beam can optionally be substantially collinear with an axis of a straight gas passageway 804.

As shown in the system 830 of FIG. 8B, a gas passageway 804 can also optionally include at least one reflective side surface 810 such that a beam propagating within the gas passageway 804 can reflect at least once off a side wall 810. A reflective side surface 810 can be realized by one or more of polishing, adding a reflective coating, or the like. As in the example system 800 of FIG. 8A, the gas passageway 804 can optionally have a maximum clearance distance between opposing internal surfaces (e.g. between opposing walls 810) such that the maximum clearance distance in at least one dimension is less than some multiple (e.g. less than 75 times, less than 65 times, less than 20 times, less than 10 times, less than 5 times, or other values noted elsewhere herein, etc.) of a characteristic dimension of the beam. At least in the case of a beam 102 that is reflected at least once from the side walls 810 and/or from a reflector at an end of the sample cell (e.g. at in FIG. 1 through FIG. 5, etc.), the maximum clearance distance need not be perpendicular to the direction of beam propagation.

A gas passageway 804 can have a cross-sectional size and shape that remain constant along its length between a first end 802 and a second end 806. Alternatively, one or more of the cross-sectional size and the cross-sectional shape can vary with distance, such as for example as shown in the system 860 of FIG. 8C. In this example, within the gas passageway 804, at least one location can include a maximum clearance distance between opposing internal surfaces of or other flow restricting features within the gas passageway 804 such that the maximum clearance distance is defined as a multiple of a characteristic dimension of the beam. The characteristic dimension of the beam can optionally be a characteristic dimension perpendicular to the axis of beam propagation. In one example, the maximum clearance distance can be less than 10 times the characteristic dimension of the beam, and this maximum clearance distance can occur at least once along the length of the gas passageway 804, for example via one or more baffle features 812 or other projections into the volume of the gas passageway 804. In other implementations of the current subject matter, the maximum clearance distance can occur two or more times (e.g. using multiple baffles 812 or other inserts or features of the sample cell walls or other structure) but not continuously along either a gas passageway 804 such as those shown in FIG. 8A, FIG. 8B, or FIG. 8C or in a multi-pass sample cell such as those shown in FIG. 1 through FIG. 5, or in other sample cells consistent with implementations of the current subject matter. While the baffle features 812 in FIG. 8C are illustrated as having a triangular shape, this aspect is merely illustrative. Other shapes are within the scope of the current subject matter.

Baffle features 812 or other sample cell shapes or features incorporating a cross-sectional area that varies along a flow direction within the sample cell can be included in a sample cell such that the maximum clearance distance discussed above occurs at least at one location within the sample cell. Such shapes or features can be useful in modifying the flow regime within a sample cell such that a faster exchange and gas concentration equilibration can be achieved. Without being bound by theory, it is possible that the use of one or more baffle features can cause the internal volume of the sample cell to have a flow regime more similar to several smaller CFSTR-modeled volumes in series, each of which can equilibrate to a new inlet concentration more quickly than a single large, well-mixed volume. Another possibility is that changes in the hydraulic diameter of a sample cell with distance along the direction of flow can result in nozzle effects, which can improve flushing of the sample cell.

Implementations of the approach described herein can be applicable to any laser spectrometer, including but not limited to spectrometers based on measurements of absorption of radiation from a tunable laser source. Examples of such spectrometers include direct absorption spectrometers, harmonic absorption spectrometers, differential absorption spectrometers, Raman spectrometers, and the like. For a direct absorption spectrometer, a measurement of concentrations of one or more trace analytes can be performed without using a harmonic conversion or demodulation of the signal obtained from the detector. However, periodic or continuous recalibration of the laser light source, detector, etc. can be performed using a calibration circuit, etc. that makes use of a harmonic signal obtained from the detector signal.

Figure 9:
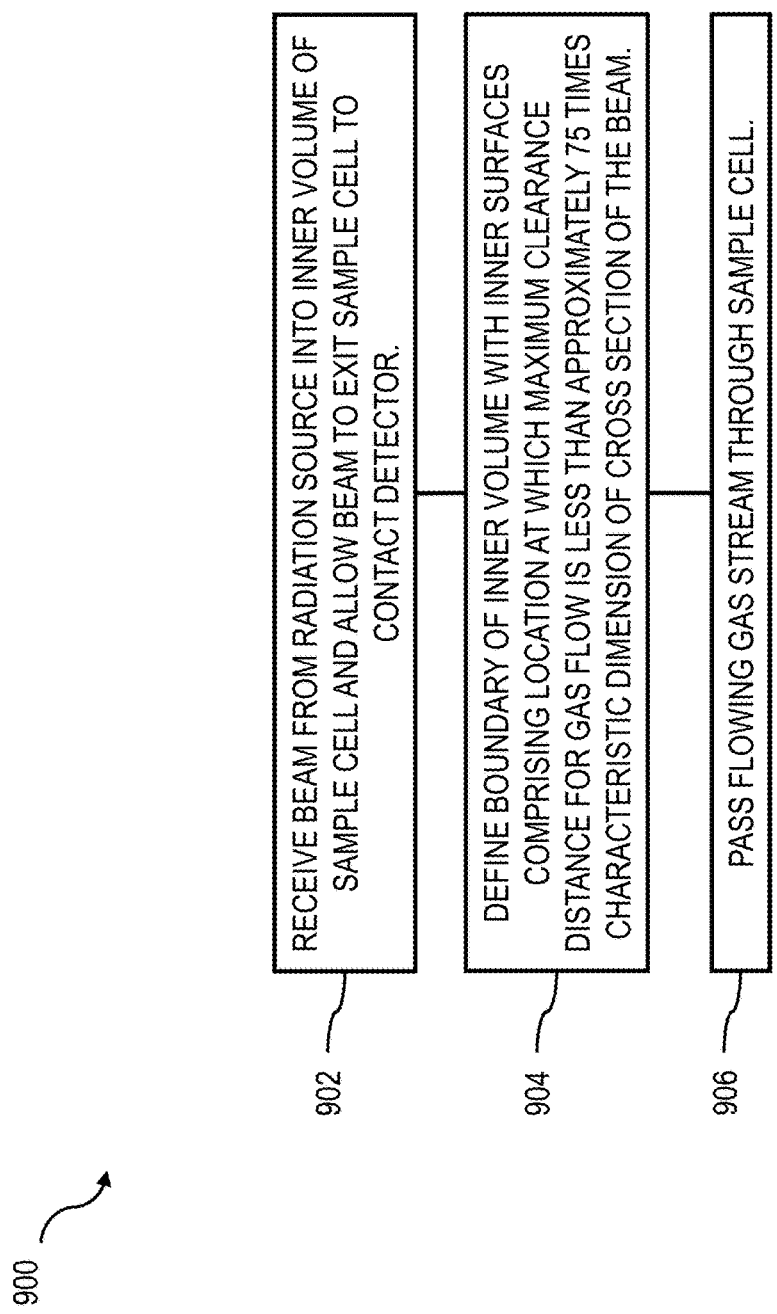
FIG. 9 shows a process flow diagram illustrating features of a method consistent with implementations of the current subject matter.

FIG. 9 shows a process flow chart 900 illustrating features of a method consistent with implementations of the current subject matter. At 902, a beam is received from a radiation source into an inner volume of a sample cell and the beam is allowed to exit the sample cell to contact a detector. The receiving and the allowing occur via at least one opening. At 904, a boundary of the inner volume is defined with inner surfaces such that the inner surfaces include at least one location at which a maximum clearance distance for gas flow is less than approximately 75 times a characteristic dimension of a cross section of the beam. At 906, a gas is passed through the sample cell.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claim.

What is claimed is:

1. A sample cell for laser absorption spectroscopy, the sample cell comprising:
   at least one opening for receiving a beam from a radiation source into an inner volume of the sample cell and for allowing the beam to exit the sample cell to contact a detector;
   an inner surface defining a boundary of the inner volume, the inner surface comprising a location at which a maximum clearance distance for gas flow between the inner surface and an opposing inner surface is less than approximately 75 times a characteristic dimension of a cross section of the beam,
   wherein the sample cell comprises a Herriott cell in which the beam traverses a distance between opposing mirrors a plurality of times between different points on the opposing mirrors with each reflection.

2. A sample cell as in claim 1, wherein the sample cell comprises an insert that occupies an excess gas volume within the inner volume through which the beam does not pass, and wherein an insert surface of the insert comprises at least part of the location.

3. A sample cell as in claim 2, wherein the insert comprises one or more of a flat insert, a conical insert, a hyperbolic insert, a trapezoidal insert, a cylindrical insert, and a hollow rod insert.

4. A sample cell as in claim 2, wherein the insert comprises a component volume configured to house one or more of an electronics component, a wiring component, a flow control component, and a scrubber component of a spectroscopy system.

5. A sample cell as in claim 2, wherein the insert comprises a gas conduit to feed gas to an inlet of the inner volume.

6. A sample cell as in claim 5, wherein the gas conduit comprises an inlet and a liquid drain that is separate from the inlet to divert liquids carried within the gas conduit away from the inner volume.

7. A sample cell as in claim 1, wherein the sample cell is configured as a tubular enclosure, a rectangular enclosure, a White cell, and a Pfund cell.

8. A sample cell as in claim 1, wherein the inner volume is at least partially contained within a gas passageway having at least one side wall and a length over which the beam travels at least once, the at least one side wall comprising the inner surface, and wherein the beam is reflected at least once from the at least one side wall as the beam travels through the gas passageway.

9. A sample cell as in claim 8, wherein the gas passageway is formed within a block by one or more of a boring process and a channeling process, and wherein the block comprises one or more parts that form the gas passageway.

10. A sample cell as in claim 8, wherein the gas passageway has a cross-sectional shape, and wherein over at least part of the length, the cross sectional shape comprises at least one of a circle, an ellipse, and a rectangle.

11. A sample cell as in claim 8, wherein the gas passageway is disposed such that the beam travels through the gas passageway from the source located near a first end of the gas passageway to the detector located near a second end of the gas passageway.

12. A sample cell as in claim 10, wherein the gas passageway is substantially collinear with an axis of propagation of the beam.

13. A sample cell as in claim 1, wherein the maximum clearance distance is in a range of approximately 3 to 10 times the characteristic dimension of the cross section of the beam or in a range of approximately 3 to 50 times the characteristic dimension of the cross section of the beam.

14. A sample cell as in claim 1, further comprising at least one reflective surface from which the beam is reflected at least one time.

15. A sample cell as in claim 14, wherein the at least one reflective surface comprises a mirror disposed at one end of the inner volume.

16. A sample cell as in claim 1, wherein the at least one location comprises at least one baffle feature that creates the maximum clearance distance for gas flow in at least one dimension.

17. A method comprising:
   receiving a beam from a radiation source into an inner volume of a sample cell and allowing the beam to exit the sample cell to contact a detector;
   defining a boundary of the inner volume with an inner surface, the inner surface comprising a location at which a maximum clearance distance for gas flow between the inner surface and an opposing inner surface is less than approximately 75 times a characteristic dimension of a cross section of the beam; and
   passing a flowing gas stream through the sample cell, wherein the sample cell comprises a Herriott cell in which the beam traverses a distance between opposing mirrors a plurality of times between different points on the opposing mirrors with each reflection.

18. A method as in claim 17, wherein the maximum clearance distance is in a range of less than approximately 65 times the characteristic dimension of the cross section of the beam.

19. A sample cell as in claim 1, wherein the characteristic dimension of a cross section of the beam is less than a diameter or width of the at least one opening.

20. A sample cell as in claim 1, wherein the characteristic dimension of a cross section of the beam is approximately 300 μm to 1000 μm.

* * * * *